United States Patent [19]

Nomura

[11] Patent Number: 5,382,689

[45] Date of Patent: Jan. 17, 1995

[54] PROCESS FOR PREPARATION OF BEVANTOLOL HYDROCHLORIDE

[75] Inventor: Yutaka Nomura, Chiba, Japan

[73] Assignee: Nippon Chemiphar Co., Ltd., Tokyo, Japan

[21] Appl. No.: 955,328

[22] Filed: Oct. 1, 1992

[30] Foreign Application Priority Data

Oct. 3, 1991 [JP] Japan .................................. 3-283875

[51] Int. Cl.⁶ ............................................ C07C 209/16
[52] U.S. Cl. .................................................. 564/349
[58] Field of Search .......................................... 564/349

[56] References Cited

U.S. PATENT DOCUMENTS 3,857,891 12/1974 Holmes et al. ...................... 564/349

Primary Examiner—Richard L. Raymond
Attorney, Agent, or Firm—McAulay Fisher Nissen Goldberg & Kiel

[57] ABSTRACT

Disclosed is a new process for preparing bevantolol hydrochloride suitable for industrial production in which bevantolol hydrochloride can be obtained in a high yield and HVA of an expensive material can be recovered. The process for the preparation of bevantolol hydrochloride comprises the steps of: causing 3-(m-tolyloxy)-1,2-epoxypropane (TOEP) to react with β-(3,4-dimethoxyphenyl)ethylamine (HVA) of excess mole per mole of said TOEP; dissolving the reaction mixture in a halogenated hydrocarbon to give a solution; mixing the solution with hydrochloric acid; separating an organic layer from the resulting mixture; and obtaining 1-[(3,4-dimethoxyphenethyl)amino]-3-(m-tolyloxy)-2-propanol hydrochloride from the organic layer.

5 Claims, No Drawings

PROCESS FOR PREPARATION OF BEVANTOLOL HYDROCHLORIDE

FIELD OF THE INVENTION

The present invention relates to a novel process for the preparation of bevantolol hydrochloride, i.e., 1-[(3,4-dimethoxyphenethyl)amino]-3-(m-tolyloxy)-2-propanol (hereinafter referred to as bevantolol) hydrochloride.

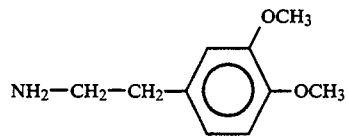

to give bevantolol of the above formula (1), the resultant bevantolol further reacts with TOEP of the starting material to produce a by-product represented by the following formula (4):

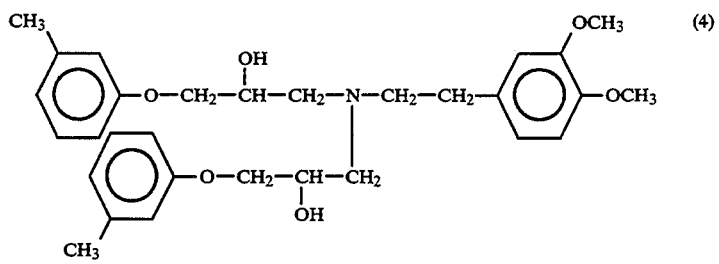

BACKGROUND OF THE INVENTION

It is known that hydrochloride of bevantolol represented by the following formula (1):

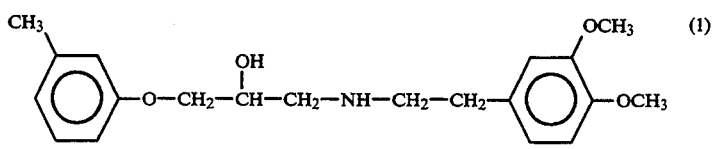

shows cardio-selective β-receptor blocking action (see U.S. Pat. No. 3,857,891, Japanese Patent Publication No. 52(1977)-33621, Japanese Patent Provisional Publication No. (1985) -246351).

A process for the preparation of above bevantolol is disclosed in Japanese Patent Publication No. 52(1977)-33621, in which 3-(m-tolyloxy)-1,2-epoxypropane (TOEP) and β-(3,4 -dimethoxyphenyl) ethylamine (HVA) are caused to react in equimolar amounts at 0 to 150° C. for 10 minutes to 24 hours. This publication has no description as to yield of the desired compound. However, in Japanese Patent Provisional Publication No. 60(1985)-246351, it is described that a trace experiment of Example 2 of the above U.S. Patent results in a yield of not more than 50 % though the yield is variable (page 7, left upper column, lines 2 to 3 in the publication). The reason of such low yield is considered as follows:

When 3-(m-tolyloxy)-1,2-epoxypropane (hereinafter referred to as TOEP) represented by the following formula (2):

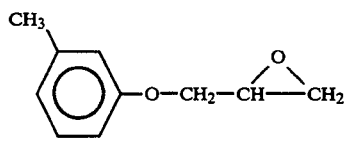

reacts with β-(3,4 -dimethoxyphenyl) ethylamine (hereinafter referred to as HVA) represented by the following formula (3):

Such consumption of the produced bevantolol causes its low yield.

Japanese Patent Provisional Publication No. 60(1985)-246351 discloses a process for preparing bevantolol comprising the steps of bringing the compound of the above formula (2) into contact with the compound of the above formula (3) in equimolar amounts, and adding a small amount of a seed of bevantolol to the reaction mixture. In the process, the obtained bevantolol is taken off from the reaction mixture by the addition of the seed for crystallization and the produced bevantolol is kept from reacting with TOEP of the starting material. By the procedure, it is intended that a yield of the bevantolol is increased. However, the process needs a long period of time in the adding procedure and the mixing procedure (Example 2 of the above-mentioned publication describes that it takes a period of time of not shorter than 100 hours from the mixing of starting materials to obtaining bevantolol). Further, the initial contact between TOEP and HVA is required to perform under cooling.

SUMMARY OF THE INVENTION

It is an object of the present invention to provide a process for the preparation of bevantolol hydrochloride suitable for industrial production in which bevantolol hydrochloride can be obtained in a high yield and HVA of an expensive material can be recovered.

There is provided by the invention a process for the preparation of bevantolol hydrochloride comprising the steps of:
  causing 3-(m-tolyloxy)-1,2-epoxypropane (TOEP) to react with β-(3,4-dimethoxyphenyl)ethylamine (HVA) of excess mole per mole of said TOEP;
  dissolving the reaction mixture in a halogenated hydrocarbon solvent to give a solution;
  mixing the solution with hydrochloric acid;

separating an organic layer from the resulting mixture.

Preferred embodiments of the process for the preparation of bevantolol hydrochloride according to the present invention are as follows:

1) The process for the preparation of bevantolol hydrochloride, wherein the molar amount of said β-(3,4dimethoxyphenyl)ethylamine per 1 mole of said 3-(m-tolyloxy)-1,2-epoxypropane is in the range of 1.5 to 5.5 moles.

2) The process for the preparation of bevantolol hydrochloride, wherein said halogenated hydrocarbon solvent is chloroform or dichloromethane.

3) The process for the preparation of bevantolol hydrochloride, wherein said reaction is conducted at a temperature in the range of 0 to 150° C.

4) The process for the preparation of bevantolol hydrochloride, wherein after said resulting mixture is separated into an organic layer and an aqueous layer, 1-[(3,4-dimethoxyphenethyl)amino]-3-(m-tolyloxy)-2-propanol hydrochloride is obtained from the organic layer and said β-(3,4-dimethoxyphenyl)ethylamine (HVA) is recovered from the aqueous layer.

In accordance with the present invention, formation of by-product of the above formula (4) is prevented by causing TOEP to react with HVA in excess amount compared with a stoichiometric amount to the TOEP, so that bevantolol hydrochloride can be obtained in a high yield and HVA of an expensive material can be recovered. Accordingly, the process for the preparation of bevantolol hydrochloride of the invention is suitable for industrial production.

DETAILED DESCRIPTION OF THE INVENTION

TOEP and HVA of the starting materials employed in the invention, and bevantolol hydrochloride of the product of the invention are known.

In the invention, HVA first is mixed with TOEP in excess mole per mole of TOEP. The molar amount of HVA per 1 mole of TOEP preferably is in the range of 1.5 to 5.5 moles, more preferably is in the range of 2.5 to 3.5 moles. The mixture is caused to react at a temperature in the range of 0 to 150° C., preferably at room temperature for 20 to 60 hours or at 70 to 90° C. for 3 to 10 hours. The reaction is preferably conducted in a stream of nitrogen. In the case that the molar ratio of HVA to TOEP is less than the lower limit of the above range, the by-product of the formula (4) increases and yield of bevantolol decreases. In the case that the molar ratio is more than the upper limit of the range, the amount of recovery of expensive HVA is reduced. Further, in the case that the reaction temperature is lower than the above range, the reaction is too time-consuming for an industrial process. In the case that the reaction temperature is higher than the above range, the yield of bevantolol decreases owing to occurrence of side reaction.

The above reaction is preferably carried out in the absence of a solvent. However, the reaction may be conducted using a solvent such as cyclohexane, chloroform, dichloromethane or isopropyl alcohol unless the solvent gives adverse effects to the reaction. When the solvent is used in the reaction, the reaction solution is preferably concentrated after the reaction is complete.

In the invention, the reaction mixture (containing bevantolol) is dissolved in a halogenated hydrocarbon solvent. Preferred examples of the halogenated hydrocarbon solvents include chloroform and dichloromethane. Particularly preferred is chloroform. The amount of the halogenated hydrocarbon varies with the amount of HVA and hydrochloride, but is generally preferred in the range of 3 to 15 ml per 1 g of bevantolol to be produced. For example, when chloroform is used as the halogenated hydrocarbon, the chloroform preferably is in the range of 5 to 7 ml per 1 g of bevantolol.

Subsequently, to the resultant solution containing the bevantolol is added hydrochloric acid, and the solution is sufficiently stirred at room temperature to convert the bevantolol and HVA into a hydrochloride salt thereof. Then, the above mixture is allowed to stand to separate an organic layer containing bevantolol hydrochloride from an aqueous layer containing HVA hydrochloride. The hydrochloric acid is added in an amount to make the aqueous layer acidic. The required amount of hydrochloric acid can be confirmed by measuring pH of the aqueous layer.

The bevantolol hydrochloride is obtained from the organic layer by conventional procedures, for example, a process comprising the steps of evaporating the halogenated hydrocarbon from the organic layer under reduced pressure, crystallizing bevantolol hydrochloride by treating the residue with an appropriate solvent such as isopropyl alcohol or acetonitrile, and if necessary, further purifying bevantolol hydrochloride by recrystallizing it from an appropriate solvent such as isopropyl alcohol.

In accordance with the invention, bevantolol hydrochloride can be obtained in a high yield of not less than 70% within a short period of time. To the aqueous layer separated above is added a base such as an alkali metal hydroxide to make the layer alkaline of not less than pH 11. This alkaline aqueous solution is treated with an organic solvent such as toluene or chloroform, and an organic layer is separated. The solvent is distilled off from the organic layer. The resulting residue is then placed under reduced pressure to recover unreacted HVA. In this manner, the unreacted HVA can be recovered in a high yield and then can be employed for the next reaction, repeatedly.

Examples of the present invention are given below, whereby the invention is explained in more detail.

EXAMPLE 1

In a flask equipped with a stirrer were introduced 1.64 g (10.0 mmol.) of TOEP and 5.44 g (30.0 mmol.) of HVA in a stream of nitrogen, and they were heated under sufficiently stirring at 80±5° C. for 6 hours. The reaction mixture was cooled, and 15 ml of chloroform was placed in the flask to dissolve the mixture. 30 ml of 2N hydrochloric acid was added to the resultant solution, and they were mixed under vigorous stirring. Then, the mixture was allowed to stand to separate an organic layer from an aqueous layer. The organic layer was taken out from the flask. 5 ml of chloroform was added to the aqueous layer and they were stirred vigorously. Then, an organic layer was separated from an aqueous layer. The resultant two organic layers were combined and dried over anhydrous sodium sulfate. The dried organic layer was filtered to remove the sodium sulfate, and the chloroform in the mixture was evaporated. The obtained residue was dissolved in 20 ml of isopropyl alcohol under heating and then cooled with stirring under atmospheric conditions. Precipitated crystals were collected on a filter, washed with 20 ml of isopropyl alcohol and dried to give 3.08 g (yield: 80.8%) of crude crystals of bevantolol hydrochloride.

The crude crystals were dissolved in 18.5 ml of isopropyl alcohol under heating, and cooled with stirring under atmospheric conditions. Precipitated crystals were collected on a filter, washed with 18 ml of isopropyl alcohol and dried to give 2.82 g (yield: 74.0%) of purified crystals of bevantolol hydrochloride (m.p. 140–143 °C.).

To the aqueous layers separated from the chloroform layer was added aqueous 6N sodium hydroxide to make the solution alkaline of pH 11 or higher. The resulting alkaline solution was extracted with two 30 ml portions of chloroform. The resultant two organic layers were combined, dried over anhydrous sodium sulfate and then placed under reduced pressure to distill off chloroform. The obtained residue was subjected to distillation under reduced pressure to give 3.33 g (18.4 mmol.) of HVA.

EXAMPLE 2

The procedure of Example 1 was repeated except for changing the amount of HVA to 4.53 g (25 mmol.), to obtain 2.92 g (yield: 76.6%) of crude crystals of bevantolol hydrochloride.

The aqueous layers separated from the chloroform solution were subjected to the same treatment as that of Example 1 to recover HVA.

EXAMPLE 3

The procedure of Example 1 was repeated except for changing the temperature of reaction of TOEP and HVA to room temperature and the reaction time to 48 hours, to obtain 3.08 g (yield: 80.8%) of crude crystals of bevantolol hydrochloride.

The aqueous layers were subjected to the same treatment as that of Example 1 to recover HVA.

EXAMPLE 4

The procedure of Example 1 was repeated except for adding 5 ml of cyclohexane to TOEP and HVA, and changing the reaction temperature to room temperature and the reaction time to 48 hours, to obtain 2.95 g (yield: 77.4%) of crude crystals of bevantolol hydrochloride.

The aqueous layers were subjected to the same treatment as that of Example 1 to recover HVA.

EXAMPLE 5

The procedure of Example 1 was repeated except for changing the amounts of TOEP and HVA to 8.20 g (50 mmol.) of TOEP and 45.25 g (250 mmol.) of HVA, adding 75 ml of chloroform to TOEP and HVA, conducting the reaction for 5.5 hours under reflux, changing 2N hydrochloric acid to 4N hydrochloric acid, and using 100 ml of acetonitrile as the crystallization solvent, to obtain 15.42 g (yield: 80.8%) of crude crystals of bevantolol hydrochloride.

The aqueous layers were subjected to the same treatment as that of Example 1 to recover 34.42 g (190 mmol.) of HVA.

EXAMPLE 6

The procedure of Example 1 was repeated except for changing the amounts of TOEP and HVA to 1.64 g (10 mmol.) of TOEP and 9.05 g (50 mmol.) of HVA, adding 15 ml of isopropyl alcohol to TOEP and HVA, conducting the reaction for 1 hour under reflux, and using 20 ml of acetonitrile as the crystallization solvent, to obtain 2.89 g (yield: 75.8%) of crude crystals of bevantolol hydrochloride.

The aqueous layers were subjected to the same treatment as that of Example 1 to recover 5.80 g (32 mmol.) of HVA.

I claim:

1. A process for the preparation of bevantolol hydrochloride comprising the steps of:

reacting 3-(m-tolyloxy)-1,2-epoxypropane with β-(3,4-dimethoxyphenyl)ethylamine in a mole ratio of 1.5 to 5.5 moles of B-(3,4-dimethoxyphenyl)ethylamine per mole of 3-(m-tolyloxy)- 1,2-epoxypropane;

dissolving the reaction mixture in a halogenated hydrocarbon solvent to give a solution;

mixing the solution with hydrochloric acid;

separating an organic layer from the resulting mixture; and obtaining 1-3-(m-tolyloxy)-2-propanol hydrochloride from the organic layer.

2. The process of claim 1 wherein the molar ratio is 2.5 to 3.5 mole of β-(3,4-dimethoxyphenyl)ethylamine per mole of 3-(m-tolyloxy )- 1,2-epoxypropane.

3. The process for the preparation of bevantolol hydrochloride as claimed in claim 1, wherein said halogenated hydrocarbon solvent is chloroform or dichloromethane.

4. The process for the preparation of bevantolol hydrochloride as claimed in claim 1, wherein said 3-(m-tolyloxy)-1,2-epoxypropane is reacted with said β-(3,4-dimethoxyphenyl)ethylamine at a temperature in the range of 0° to 150° C.

5. The process for the preparation of bevantolol hydrochloride as claimed in claim 1, wherein after said resulting mixture is separated into an organic layer and an aqueous layer, 1-3-(m-tolyloxy)-2-propanol hydrochloride is obtained from the organic layer and said β-(3,4-dimethoxyphenyl)ethylamine is recovered from the aqueous layer.

* * * * *